| United States Patent [19] | [11] Patent Number: 4,885,375 |
| Wynberg et al. | [45] Date of Patent: Dec. 5, 1989 |

[54] RESOLUTION OF 3-(4-METHOXYPHENYL)GLYCIDIC ACID WITH IN SITU CONVERSION TO ALKYL ESTERS

[75] Inventors: Hans Wynberg, Groningen; Wolter ten Hoeve, Eelde, both of Netherlands

[73] Assignee: Marion Laboratories, Inc., Kansas City, Mo.

[21] Appl. No.: 195,749

[22] Filed: May 18, 1988

[51] Int. Cl.$^4$ .......................................... C07D 303/18
[52] U.S. Cl. .................................................. 549/557
[58] Field of Search ........................................ 549/557

[56] References Cited

U.S. PATENT DOCUMENTS 4,416,819 11/1983 Nagao et al. ...................... 540/491
4,520,203 5/1985 Abraham et al. .................... 548/432

FOREIGN PATENT DOCUMENTS 60-013775 1/1985 Japan .
60-013776 1/1985 Japan .

OTHER PUBLICATIONS

Roberts et al., "An Introduction to Modern Experimental Organic Chemistry, Second Edition," Holt, Rinehart and Winston, Inc., New York, NY, (1974), pp. 7–11.
Rudy, C. J., M.A., Thesis, Western Michigan University, Kalamazoo, MI (1985), pp. 56–58.
J. March, "Advanced Organic Chemistry," 2nd ed., pp. 367–368 (1977).
J. Grundy, et al. *Tetrahedron Letters* (1972), "Esterification of Sterically Hindered Carboxylic Acids Using Dimethyl Sulphate," pp. 757–758.

*Primary Examiner*—Glennon H. Hollrah
*Assistant Examiner*—Mark W. Russell
*Attorney, Agent, or Firm*—Christopher John Rudy

[57] ABSTRACT

Optically active 3-(4-methoxyphenyl)glycidic acid alkyl esters of high enantiomeric purity can be prepared through optical resolution of a racemic or optically enriched sample of a 3-(4-methoxyphenyl) glycidic acid. The alkali metal salt of the acid, generated in situ by hydrolysis of the corresponding alkyl ester with an alkali metal hydroxide is contacted with a suitable resolving agent such as an optically pure amine to form the corresponding diastereomeric salts. The desired diastereomeric salt is separated from the mixture and transformed to an alkali metal salt, which optionally without isolation is converted into the desired alkyl ester of high enantiomeric purity.

17 Claims, No Drawings

RESOLUTION OF 3-(4-METHOXYPHENYL)GLYCIDIC ACID WITH IN SITU CONVERSION TO ALKYL ESTERS

FIELD

This invention concerns resolution of 3-(4-methoxyphenyl)glycidic acid. The glycidates are useful intermediates in the synthesis 1,5-benzothiazepines.

BACKGROUND

Sawai et al., Jpn. Kokai Tokkyo Kojo No. 60-13775 (Jan. 24, 1985), and Sawai et al., Jpn. Kokai Tokkyo Kojo No. 60-13776 (Jan. 24, 1985), disclose a method of producing optically active alkali metal salt 3-(p-alkoxyphenyl)glycidate and a method of producing optically active 3-(p-alkoxyphenyl)glycidic acid derivatives. Sawai et al. '776, for example, reports that d-or 1-3-(p-methoxyphenyl)glycidic acid methyl esters are oily materials having the specific rotation $[\alpha]^{22}$ of the (-) or (+) isomer of ca. 180° at a concentration of 0.5 in ethanol.

SUMMARY

The present invention provides in one aspect, a method comprising contacting a racemic or optically enriched sample of a 3-(4-methoxyphenyl)glycidic acid alkyl ester with an alkali metal hydroxide in a protic liquid medium at a low temperature, then contacting same with a suitable resolving agent to form the corresponding diastereomeric salts, separating the desired diastereomeric salt from the mixture, and transforming at least one of the diastereomeric salts to corresponding ester by converting diastereomeric salt into corresponding alkali metal salt and then alkylating the corresponding alkali metal salt with a suitable alkylating agent under conditions such that 3-(4-methoxyphenyl)glycidic acid alkyl ester of high enantiomeric purity is prepared. Another aspect is an essentially enantiomercially pure dextrorotary or levorotary 3-(4-methoxyphenyl)glycidic acid alkyl ester.

The invention provides useful chemical intermediates, especially for preparation of 1,5-benzothiazepines. The following salient advantages attend this invention:

1. The in situ preparation of the potassium salt of the acid is from the racemic ester or optically enriched ester.
2. There is no isolation of the free glycidic acid (It is very unstable.), but there is in situ conversion to diastereomeric salt, to the alkali metal salt, and thence, in situ, to the alkyl ester.
3. The virtually pure diastereomeric salt crystallizes from the solution in high yield. There is no need for further purification.

ILLUSTRATIVE DETAIL

In the practice of this invention, the optically enriched or the racemic sample of the 3-(4-methoxyphenyl)glycidic acid alkyl ester can be obtained or can be prepared by known methods or methods analogous thereto. See generally, Sawai et al., both supra, Nagao et al., U.S. Pat. No. 4,416,819 (Nov. 22, 1983).

In general herein, alkyl groups are separately at each occurrence saturated hydrocarbyl, to include $C_{1-6}$ or $C_{1-4}$ alkyl. Methyl is preferred.

Alkali metals include Li, Na, K, Rb & Cs, especially Li, Na, K. Potassium is preferred.

An excess of the hydroxide to the ester is typically used. For instance, the excess can be a molar ratio of hydroxide to ester of about 1.5:1.

Protic liquid media include water and alcohols. A preferred protic liquid medium for the first mentioned protic-media required step herein is methanol.

Low temperatures herein are those generally below 10° C., especially from about −5° to 5° C. Low temperatures are employed in view of the unstable acid. Too low a temperature slows the rate of reaction undesirably.

Time of reaction of this first step may vary. Typical times may be found within about 1 to 3 hours, especially about 2 hours.

The suitable resolving agent may illustratively be selected from among a variety of amines with optical activity. Typical examples include $\alpha$-methylbenzylamine, $\alpha$-(1-naphthyl)ethylamine, $\alpha$(2-naphthyl)ethylamine, brucine, ephedrine, psuedo-ephedrine and so forth, but primary aralkyl amines are nicely suited.

In contacting the resolving agent with the mixture, a protic liquid medium can be employed, especially an aqueous medium. A generally non-miscible medium may be present as well, for instance, a suitable ether may be present with water media.

Suitable amounts of the resolving agent are employed. Generally stoichiometric or slight excess amounts of the resolving agent with respect to the starting ester may be employed.

Acid is added here, preferably after the mentioned contact with the resolving agent. Suitable acids include strong mineral acids, e.g., hydrochloric or sulfuric acids. The acid is preferably added slowly.

Temperatures of this second step are low.

This second step may proceed rather quickly. A time under an hour may suffice.

This second step forms the diastereomeric salts. Typically, one diastereomeric salt of the pair precipitates here.

The desired diastereomeric salt is removed from the mixture. Removal is most typically of a solid by filtration, decanting, scooping, etc. The mother liquor thus typically carries a mixture enriched with the other diastereomeric salt.

The desired diastereomeric salt is converted into the corresponding resolved glycidate alkali metal salt. Conversion is preferably carried out in a protic liquid medium, especially an alcohol. An alkali metal base is contacted with the diastereomeric salt and is allowed to react with same. Temperatures are again preferably low. Separation of the converted salt is not necessary, but may be undertaken if desired. Alkylating then follows. The alkylation can be carried out in a suitable liquid media. Suitable alkylating agents are employed such as dialkylsulfates, which can be obtained or can be prepared by known methods or methods analogous thereto.

Alkylation temperatures may vary. Ambient temperatures may be employed, as appropriate to the alkylating agent.

Times of the alkylation vary. Suitable times may be found about from 1 hour to a score (20) hours. Typical alkylation reaction times are about from 3 to 6 hours.

The 3-(4-methoxyphenyl)glycidic acid ester of high enantiomeric purity thus results. The ester generally has an optical rotation of about 190° in ethanol at a concentration of 0.05 g/10 mL ethanol, or is of a higher optical purity.

The ester can be recovered by known methods. Crystallation and filtration are typically suitable for this purpose. Drying may be carried out.

Yields of the product are very high. Yields in excess of 75% of theory are obtainable with the practice of this invention.

The following examples further illustrate the invention.

EXAMPLE 1

To an ice-water bath cooled solution of 25.1 g of potassium hydroxide in 378 mL of methanol is added 50.0 g of racemic 3-(4-methoxyphenyl)glycidic acid methyl ester, with stirring. Stirring is continued for 2 hours, and the product is filtered and is washed with cold methanol and next cold acetone and is dried under vacuum at ambient temperature, yielding 54.3 g of the corresponding racemic potassium salt. A 54.0 g sample of this salt is dissolved in 425 mL of an ice-water mixture, and the reaction vessel is cooled with an ice-water bath. A sample of 159 mL of diethyl ether is added, followed by 29.6 g of optically pure (−)-methylbenzylamine. A solution of 22 mL concentrated HCl in 193 mL of water is added dropwise over 20 minutes, and the mixture is stirred for 40 minutes after the completion of the HCl addition. The product is collected and is washed with cold diethyl ether and next cold acetone, and is dried, yielding 29.5 g of the diastereomeric salt. To an NaCl/ice-water bath cooled solution of 22.4 g of KOH in 268 mL of methanol, is added 37.7 g of the (−,−)-methylbenzylamine diastereomeric salt of 3-(4-methoxyphenyl)glycide acid, $[\alpha]_{578}^{21.5} = -116°$ (0.05008 g/10mL methanol) which is stirred for 1 hour under a nitrogen blanket, and from which is collected the solid (−)$_D$-3-(4-methoxyphenyl)glycidic acid, potassium salt, which is washed with cold methanol and cold acetone and is dried, yielding 24.4 g (88.3% of theory). Next, to a stirred mixture of 10.5 g of this (−)-potassium salt in 51 mL of dimethylformamide (dried over 4 Angstrom molecular sieves) at ambient temperature under a nitrogen blanket, is added all at once, a 5.0 mL aliquot of ambient temperature dimethylsulfate (Aldrich). After a brief rise of temperature to 32° C., the temperature of the mixture drops back to ambient. Stirring is continued, and after about 4¾ hours from the addition, the mixture is cooled in an ice-water bath. Next, 51 mL of cold water is added to the mixture over a two-minute period. The aqueous mixture at 5° C. s seeded with a small quantity of (−)$_{578}$-trans-3-(4-methoxyphenyl)glycidic acid methyl ester crystals, causing instant crystallization. Upon waiting 10 minutes, the desired solid is collected by filtration and is dried under vacuum at ambient temperature, which affords 7.58 g of solid. The solid is recrystallized from 80 mL of 82:1 ethanol to water mixture, by volume, which is heated to 65° C. and is next allowed to stand under ambient temperature conditions. Upon the passage of 2¾ hours, the last hour of which is with stirring, solid is collected and is rinsed with ca. 35 mL of ambient temperature 82:1 ethanol to water mixture, yielding 5.16 g (-)$_D$-3-(4-methoxyphenyl)glycidic acid methyl ester; $[\alpha]^{22} = -212.2°$ (0.05041 g/10 mL methanol); m.p.=89.2° C. A second crop, 1.05 g, is obtained from the mother liquor; $[\alpha]_{578}^{22} = -212.3°$ (0.05049 g/10 mL methanol); $[\alpha]^{22} = -196.2°$ (0.0524 g/10 mL ethanol); m.p.=89.1° C. The product is stored under refrigeration.

EXAMPLE 2

The procedure of Example 1 is repeated except using (+)-methylbenzylamine. $[\alpha]_{578}^{20} = +213.0°$ (0.1244 g/25 mL methanol); $[\alpha]^{22} = +198.5°$ (0.0523 g/10 mL ethanol). Epilogue The present invention is thus provided. Various modifications can be effected by those skilled in the art within the spirit of this invention, the scope of which is particularly pointed out by the following distinctly claimed subject matter.

What is claimed is:

1. A method comprising contacting a racemic or optically enriched sample of a 3-(4-methoxyphenyl)glycidic acid alkyl ester with an alkali metal hydroxide in a protic liquid medium at a low temperature, then contacting same with a suitable resolving agent, then adding a suitable acid to the foregoing mixture, at a low temperature, to form the corresponding diastereomeric salts, separating desired diastereomeric salt from the mixture, and transforming at least one of the diastereomeric salts to corresponding ester by converting diastereomeric salt into corresponding alkali metal salt by contacting the diastereomeric salt with an alkali metal base and then akylating the corresponding alkali metal salt with a suitable alkylating agent, by steps under conditions such that 3-(4-methoxyphenyl)glycidic acid alkyl ester of high enantiomeric purity is prepared.

2. The method of claim 1, wherein the optically active ester is recovered as essentially enantiomerically pure.

3. The method of claim 7, wherein the glycidic acid ester alkyl moieties are $C_{1-4}$ alkyl.

4. The method of claim 3, wherein the resolving agent is an optically pure methylbenzylamine; the acid alkylating agent is dimethyl sulfate and the alkyl moieties are methyl.

5. The method of claim 4, wherein the prepared ester has an optical rotation of about, $[\alpha]^{22} = -190$ degrees, in ethanol at a concentration of 0.05 g/10 mL ethanol, or is of a higher optical purity.

6. The method of claim 4, wherein the prepared ester has an optical rotation of about, $[\alpha]^{22} = +190$ degrees, in ethanol at a concentration of 0.05 g/10 mL ethanol, or is of a higher optical purity.

7. The method of claim 2, wherein the prepared ester has an absolute optical rotation corresponding to that of methyl ester, with the absolute optical rotation of said methyl ester being about, $[\alpha]^{22} = 190$ degrees, in ethanol at a concentration corresponding to 0.05 g of said methyl ester/10 mL ethanol, or is of higher optical purity.

8. The method of claim 3, wherein the prepared ester has an absolute optical rotation corresponding to that of methyl ester, with the absolute optical rotation of said methyl ester being about, $[\alpha]^{22} = 190$ degrees, in ethanol at a concentration corresponding to 0.05 g of said methyl ester/10 mL ethanol, or is of higher optical purity.

9. The method of claim 1, wherein yield of the prepared ester is greater than 75 percent of theory.

10. The method of claim 2, wherein yield of the prepared ester is greater than 75 percent of theory.

11. The method of claim 3, wherein yield of the prepared ester is greater than 75 percent of theory.

12. The method of claim 4, wherein yield of the prepared ester is greater than 75 percent of theory.

13. The method of claim 5, wherein yield of the prepared ester is greater than 75 percent of theory.

14. The method of claim 6, wherein yield of the prepared ester is greater than 75 percent of theory.

15. The method of claim 7, wherein yield of the prepared ester is greater than 75 percent of theory.

16. The method of claim 8, wherein yield of the prepared ester is greater than 75 percent of theory.

17. In a process for preparing an optically enriched or enantiomerically pure 3-(4-methoxyphenyl)glycidic acid or corresponding alkali metal salt thereof from a starting material of an alkali metal salt of 3-(4-methoxyphenyl)glycidic acid and through use of an amine resolving agent for forming a diastereomeric salt of amine resolving agent and 3-(4-methoxyphenyl)glycidic acid residues, the improvement comprises contacting said starting material with said resolving agent in a protic medium, at a temperature generally below 10 degrees C., followed by addition of a suitable acid thereto, at a temperature generally below 10 degrees C., to form said diastereomeric salt.

* * * * *